United States Patent
Banville et al.

(10) Patent No.: US 9,248,304 B2
(45) Date of Patent: Feb. 2, 2016

(54) DEFIBRILLATOR WITH OVERRIDABLE CPR-FIRST PROTOCOL

(75) Inventors: Isabelle Banville, Sammamish, WA (US); David R. Hampton, Woodinville, WA (US); Gregory T. Kavounas, Kirkland, WA (US); Richard C. Nova, Kirkland, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 481 days.

(21) Appl. No.: 13/085,053

(22) Filed: Apr. 12, 2011

(65) Prior Publication Data

US 2011/0190836 A1    Aug. 4, 2011

Related U.S. Application Data

(62) Division of application No. 11/044,871, filed on Jan. 26, 2005, now Pat. No. 7,937,146.

(51) Int. Cl.
*A61N 1/39* (2006.01)

(52) U.S. Cl.
CPC ........................................ *A61N 1/39* (2013.01)

(58) Field of Classification Search
CPC ........ A61B 5/74; A61B 5/7405; A61B 5/742; A61B 5/7435; A61B 5/7475; A61B 5/749; A61N 1/046; A61N 1/0492; A61N 1/06; A61N 1/36014; A61N 1/39; A61N 1/3987; A61N 1/3993

USPC ................................................................ 607/5
See application file for complete search history.

(56) References Cited

U.S. PATENT DOCUMENTS

| | | | | |
|---|---|---|---|---|
| 6,314,320 B1* | 11/2001 | Powers et al. | | 607/5 |
| 6,334,070 B1* | 12/2001 | Nova et al. | | 607/5 |
| 2003/0088284 A1* | 5/2003 | Daynes et al. | | 607/5 |
| 2003/0195567 A1* | 10/2003 | Jayne et al. | | 607/5 |
| 2010/0114218 A1* | 5/2010 | Heath | | 607/5 |

* cited by examiner

*Primary Examiner* — Christopher D Koharski
*Assistant Examiner* — Frances Oropeza
(74) *Attorney, Agent, or Firm* — Marger Johnson

(57) ABSTRACT

Methods and apparatus are provided for determining a defibrillation treatment protocol in an external defibrillator whereby a user may override a CPR-first default protocol. The method includes following steps configured in a defibrillator controller of issuing an inquiry; waiting for a response to the inquiry for a set time; ordering a CPR treatment protocol if no response is received within the set time; analyzing a response; ordering a CPR treatment protocol upon receiving a non-affirmative response to the inquiry; and ordering a shock treatment protocol upon receiving an affirmative response to the inquiry. Upon selecting a shock treatment protocol, the defibrillator performs a shock analysis under the shock treatment protocol, and either orders a CPR treatment protocol if shock treatment is not indicated by the shock analysis or provides a defibrillation shock if shock treatment is indicated by the shock analysis. Queries may be presented to a user in visual, audible, or both visual and audible format.

14 Claims, 4 Drawing Sheets

DEFIBRILLATOR WITH OVERRIDABLE CPR-FIRST PROTOCOL

This application is a Divisional of U.S. application Ser. No. 11/044,871, filed Jan. 26, 2005, which published as Publication No. 2006/0167505 on Jul. 26, 2006, the entire content of which is hereby incorporated by reference.

FIELD OF THE INVENTION

The present invention generally relates to external defibrillators including AEDs and manual defibrillators, and more particularly relates to interactive defibrillators having CPR prompts for patient treatment.

BACKGROUND OF THE INVENTION

A normal human heart pumping pattern is called a sinus rhythm, and is regulated by the body's biological pacemaker within the upper right chamber of the heart, which is commonly referred to as the right atrium. This natural pacemaker, which is generally referred to as the sinoatrial (SA) node, sends electrical signals to the right and left ventricular muscles in the lower chambers of the heart. The ventricular muscles then execute the pumping action under control of the SA node. The right ventricular muscle pumps blood to the lungs for oxygenation, and the left ventricular muscle pumps the oxygenated blood to various parts of the body.

In certain circumstances, the normal or sinus heartbeat rhythm may be adversely affected as a result of some type of malfunction in the heart's electrical control system. When this type of malfunction occurs, an irregular heartbeat may result, causing the ventricular muscles to pump ineffectively, thus reducing the amount of blood pumped to the body. This irregular heartbeat is generally referred to as an arrhythmia and can lead to Sudden Cardiac Arrest (SCA).

It is estimated that approximately two hundred and twenty-five thousand (225,000) deaths per year are attributable to SCA. A particularly serious type of SCA is known as Ventricular Fibrillation (VF), which is a malfunction characterized by rapid, uncoordinated cardiac movements replacing the normal contractions of the ventricular muscles. In this event, the ventricular muscles are not able to pump blood out of the heart, and there is no initiation of a heartbeat. VF rarely terminates spontaneously, and is therefore a leading cause of sudden cardiac death. The unpredictability of VF and other irregular heart beat conditions exacerbates the problem, and emphasizes the need for early therapeutic intervention to prevent the loss of life.

Defibrillators are devices for providing life-saving electrical shock therapy to persons experiencing an irregular heat beat, such as VF. A defibrillator provides an electrical shock to the heart, in order to convert the irregular heart beat to a normal sinus rhythm. One type of defibrillator, an implantable cardioverter defibrillator (ICD), is surgically implanted in patients who are considered likely to need electrical shock therapy, precluding the necessity of constant monitoring by medical personnel.

Another commonly used type of defibrillator is the external defibrillator, which sends electrical shock pulses to the patient's heart through external electrodes applied to the patient's chest. External defibrillators may be manually operated, as are typically used in hospitals by medical personnel or may be semi-automatic, semi-automated, fully automatic, or fully automated devices, where they can be used in any location where an unanticipated need may occur. An automatic external defibrillator is commonly referred to as an AED.

It is well known that time is an important factor in the successful application of electrical shock therapy. The survival rate of persons suffering from ventricular fibrillation decreases by about ten percent (10%) for each minute the administration of a defibrillation shock is delayed. It is therefore desirable to minimize the time duration between powering up an external defibrillator and administering the electrical shock therapy to the patient. It is also estimated that the rate of survival for SCA victims averages less than two percent (2%) when defibrillation is delayed ten (10) minutes or more.

In a typical usage of a defibrillator, the defibrillator electrodes are attached to the patient prior to delivery of a defibrillation shock. The defibrillator can also monitor the patient's condition and physiological parameters. This data can be measured and analyzed, and then an appropriate therapy determined. If a shock is recommended, the defibrillator charges to an appropriate level and applies the shock therapy in a desired format. One or more of these activities can be done by medical/emergency personnel, as in the case of manual defibrillators, or by an automatic or automated process, as in the case of automatic, semi-automatic, automated and semi-automated defibrillators. These actions, while necessary, can be disadvantageously time-consuming, and can delay the administration of the shock therapy.

Additionally, some defibrillators integrate cardiopulmonary resuscitation (CPR) instructions along with shock treatment. CPR is a combination of techniques including artificial respiration (rescue breathing) and artificial circulation (chest compression). One purpose of CPR is to provide oxygenated blood through the body, and to the brain, in those patients where a prolonged loss of circulation places the patient at risk. For example after a period of time without restored circulation, typically within four (4) to six (6) minutes, cells in the human brain can begin to be damaged by lack of oxygen. In some cases, shock therapy does not immediately restore a normal heart rhythm; several shocks may be required. In other cases, CPR should be administered prior to any defibrillation therapy. Thus, for some patients the appropriate treatment calls for a combination of shock therapy and CPR while other cases may call for shock therapy first.

Many defibrillators also include a CPR protocol. A CPR protocol typically uses voice prompts and/or a form of interactive display that guides a user in when to apply CPR methods and shock therapy. A CPR-first protocol has been proposed for use with some defibrillators. Under this protocol, the defibrillator is configured to prompt CPR as the first type of therapy to be given to a patient. In such a device the defibrillator may also include ECG (electrocardiogram) capability in order to monitor patient conditions. One example of an external defibrillator with CPR prompts is described in U.S. Pat. No. 6,356,785. Another example is described in U.S. Pat. No. 6,334,070. The CPR protocol includes prompts which indicate when CPR should be applied. The prompt may be in the form of a visual/graphical display, an audio display, or some other form of communication.

Referring now to FIG. 1 there is illustrated a flow chart that describes a CPR-first defibrillator protocol. A usage of the defibrillator begins when it is brought to the scene of an emergency and activated 2. The first action 4 of the machine is to instruct a CPR therapy to the user. After issuing the CPR instructions, and any attendant routine of queries and responses within the CPR protocol, the machine then performs an analysis 6 of the patient's ECG to determine if it is advisable to deliver a defibrillating shock 8. This analysis is referred to as "shock analysis" in this document. It is noted that in this system a CPR-first instruction is the automatic, default action of the device.

While it is advantageous to integrate CPR and shock therapy, there are instances in which CPR first, prior to shock therapy, is not the appropriate patient treatment. In these cases, shock therapy should be administered first, and any delay in doing so is potentially adverse to the patient. Nevertheless, in those systems that have a default CPR-first protocol, it is required that a user first pass through the CPR prompts in order to reach the shock treatment protocol Hence there exists a need for an improved defibrillator and an improved method for operating a defibrillator. Namely, there is a need for a defibrillator, and especially an external defibrillator, that addresses one of more of the above-noted drawbacks and limitations. It would be desired to provide a defibrillator and a control system thereof that reduces the inherent time delays associated with shock administration in external defibrillators. In addition, it would be desired to provide a defibrillator that includes convenient interactive features so that output and input can be quickly received and supplied by a human operator/user. Finally, it would be desired to provide a defibrillator that, by virtue of the foregoing, offers an improved level of response and patient treatment. The present invention addresses one or more of these needs.

BRIEF SUMMARY OF THE INVENTION

The present invention provides a defibrillator with an overridable CPR-first protocol. In one embodiment, and by way of example only, there is provided a method for selecting a treatment protocol in an external defibrillator with CPR-first set as a default treatment protocol wherein the method comprises the steps of: activating a defibrillator at an emergency scene; generating a query whether to bypass the CPR-first protocol; initiating a timer upon outputting the query that runs for a set time; ordering the CPR protocol if a response has not been received within the set time; inputting a response to the query; analyzing the response; ordering the CPR protocol if the response to the query is negative; ordering the CPR protocol if the response to the query is any response other than affirmative; ordering a shock analysis if the response to the query is affirmative; providing a defibrillation shock if the shock analysis indicates shock treatment; and ordering the CPR treatment protocol if the shock analysis indicates no shock treatment. The step of analyzing the response may occur immediately upon receiving an input response. The step of activating a defibrillator may initiate a query sequence. Additionally, the step of outputting a query may include outputting or generating a series of queries or tests. Finally, the method may include a step of overriding the query and response sequence by directing an immediate shock therapy analysis. There is additionally provided a defibrillator and a method of using the defibrillator that includes the above-described method of selecting a treatment protocol.

Other independent features, characteristics, and advantages of the defibrillator with an overridable CPR-first protocol will become apparent from the following detailed description, taken in conjunction with the accompanying drawings which illustrate, by way of example, the principles of the invention.

DETAILED DESCRIPTION

The following detailed description of the invention is merely exemplary in nature and is not intended to limit the invention or the application and uses of the invention. Furthermore, there is no intention to be bound by any expressed or implied theory presented in the preceding background of the invention or the following detailed description of the invention. Reference will now be made in detail to exemplary embodiments of the invention, examples of which are illustrated in the accompanying drawings. Wherever possible, the same reference numbers will be used throughout the drawings to refer to the same or like parts.

Figure 1:
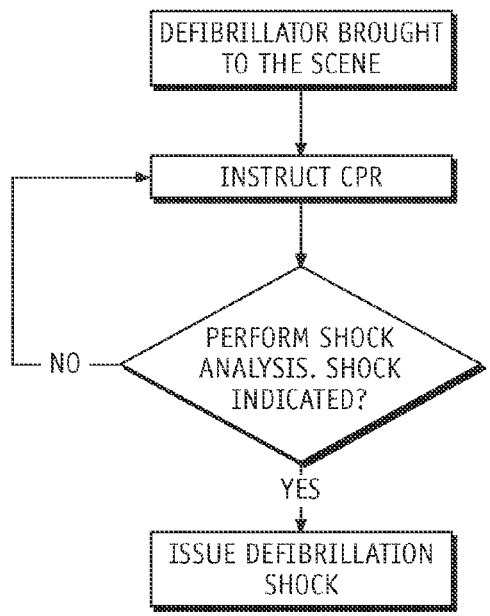
FIG. 1 is a flowchart showing a CPR-first defibrillation protocol.
Figure 2:
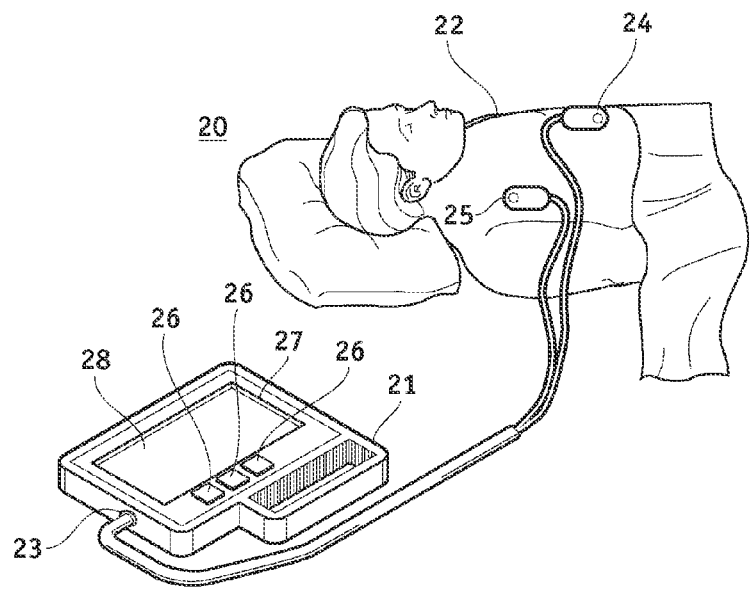
FIG. 2 is an illustration of an external defibrillator system connected to a patient in accordance with an exemplary embodiment of the present invention.

Referring now to FIG. 2 there is shown a typical defibrillator system 20 that may be used in embodiments of the present invention. The system 20 is configured to deliver a defibrillation shock to a patient 22, such as a victim of VF. The defibrillator system 20, includes, but is not limited to, an external defibrillator 21 having a connection port 23 that is configured to receive one or more electrodes (24, 25). The external defibrillator 21 can be any number of external defibrillators in accordance with the present invention. For example, the external defibrillator 21 can be an Automatic External Defibrillator or Automated External Defibrillator, semi-Automatic or semi-Automated External Defibrillator, or a manually operated external defibrillator. U.S. Pat. No. 4,610,254 to Morgan and U.S. Pat. No. 6,334,070 to Nova provide illustrative examples of defibrillators, and these two patents are hereby incorporated in their entirety by reference.

The external defibrillator 21 preferably includes a user interface 27. The interface 27 may include an output device such as a display 28 that is configured to visually present information which may include various measured or calculated parameters of patient 22 and/or other information to the operator (not shown) of the external defibrillator 21. Display 28 is capable of providing information both in textual, numeric, graphical, and/or symbolic format. Information may also be output from the defibrillator through other means such as but not limited to audible signals and/or voice prompts through a speaker or other audio generation device. When a display 28 is included, it may comprise any number of display configurations, e.g., Liquid Crystal Display (LCD) or Active Matrix Liquid Crystal Display (AMLCD). Other output devices are also possible such as LED's and other light indicators. In some embodiments, a printer may also be included for creating hard copies of data.

The user interface 27 can also include one or more input devices 26 that are configured to receive commands or information from the operator. Input devices may include, but are not limited to, devices such as keys, buttons, switches, touch screens, keyboards, and keypads. The device may also be configured to receive input electronically such as via radio signals, electrical signals, and digital transfer of information. Thus, for example, in some embodiments, the defibrillator receives input from electrodes positioned on patient 22. In one embodiment, the defibrillator is additionally configured to receive input in the form of human voice commands Thus a receiving device such as a microphone is included, along with the necessary means to convert voice signals to recognizable controller commands.

Electrodes 24, 25 are typically multifunction electrodes in that they are configured both to provide defibrillation therapy and to sense one or more physiology and/or physical parameters of the patient 22 that are received by the external defibrillator 21 at the connection port 23. This is a typical configuration in an AED type device; it will be understood by those skilled in the art that electrodes may be designed differently for different machines. Other defibrillators, including for example manual defibrillators, may also have an additional set of electrodes (not shown), in addition to the multifunction electrodes, used to receive ECG information. These additional electrodes, ECG electrodes, are generally smaller than therapeutic/multifunction electrodes, and ECG electrodes typically plug into a separate port (not shown) than the therapeutic/multifunction electrodes. As is understood in the art, ECG electrodes typically have a three wire lead, though other arrangements are possible. The signals provided by the one more electrodes (24,25) are preferably evaluated by the external defibrillator 21 to determine, among other things, whether a defibrillation shock should be applied to patient 22 in accordance with techniques known to those of ordinary skill in the art. In some embodiments this external defibrillator 21 can also evaluate the signals provided by the one more electrodes 24, 25 to determine the waveform parameters of the defibrillation shock (e.g., sinusoidal, monophasic, biphasic, truncated) as well as the shock magnitude and duration. As is understood in the art, manual defibrillators may allow for a manual selection of shock parameters.

A variety of physiological data and signals of the patient 22 can be sensed by the defibrillator through the electrodes 24, 25 or though other sensors. For example, conventional phonocardiogram (PCG) transducers can be used to convert acoustical energy of the patient's heart to electrical energy for production of a PCG waveform. Additionally, electrical activity of the patient's heart can be converted for production of an electrocardiogram (ECG) waveform. Transthoracic impedance and other physiological signals of the patient may also be detected. This data represented by this information can be collected and processed in the controller of the defibrillator. As related in more detail further on, this data may be used, for example, to determine without user input whether a CPR override is appropriate.

Figure 3:
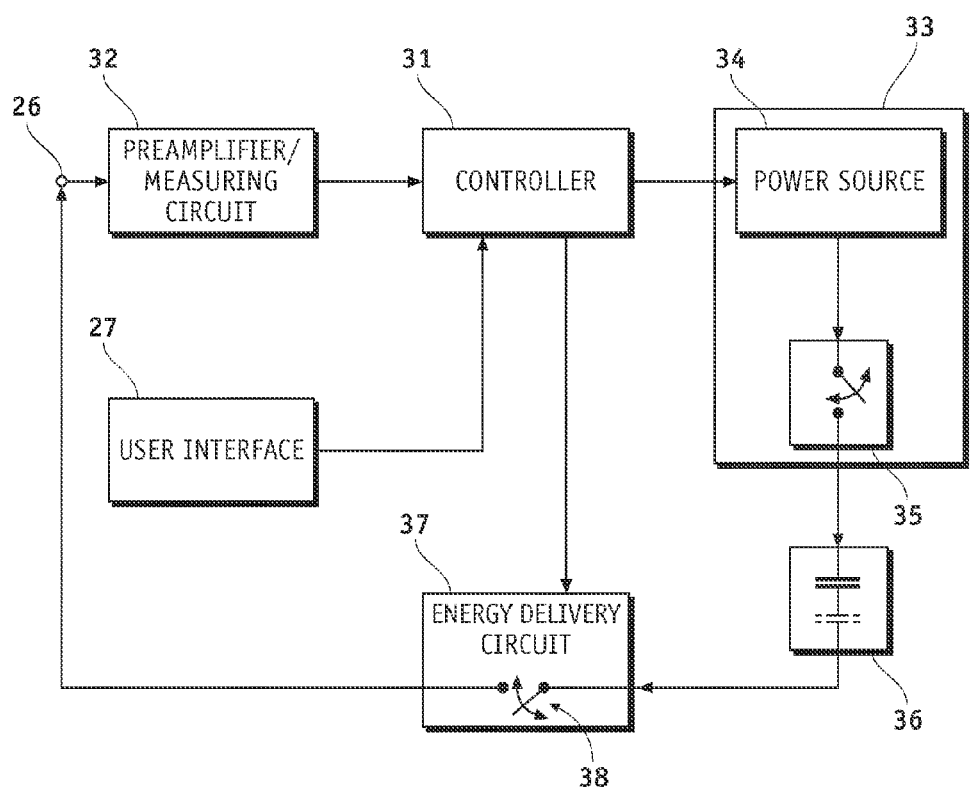
FIG. 3 is a simplified block diagram of an external defibrillator system in accordance with an exemplary embodiment of the present invention.

Referring to FIG. 3, a simplified block diagram of the external defibrillator 21 is illustrated in accordance with an exemplary embodiment of the present invention. The external defibrillator 21 preferably includes a controller 31, the user interface 27 (e.g., switches or buttons 26 and/or display 28 as shown in FIG. 2), a pre-amplifier/measuring circuit 32, a charging mechanism 33 that can include a power source 34 and a switch 35 to couple the power source 34 to the one or more energy storage devices (e.g., capacitors) 36 and an energy delivery circuit 37, which is illustrated as a switch 38 that is configured to selectively couple the one or more energy storage devices 36 to the connection port 23 under the control of the controller 31. The energy delivery circuit 37 can be implemented with any number of circuit configurations. For example, in a biphasic circuit, an H-bridge circuit can be used in accordance with the present invention. The controller 31 can be a single processing unit or multiple processing units and can be implemented with software, hardware, or a combination of hardware and software. The controller 31 is configured to at least partially control the operation of the external defibrillator 21, including control of charging the one or more energy storage devices 36. Controller 31 further controls input and output to the device, including display methods, and any sequencing of queries and responses.

An AED is generally designed for use by a "first responder," a user who would typically be the first person to arrive on the scene of a medical emergency. A first responder may be a layperson with minimal or no AED training AEDs are being made to be interactive so as to be able to provide a level of guidance to a first responder. This has been found particularly useful with those devices designed for use by laypersons, or others with minimal emergency response training. As previously stated, a CPR-first protocol is being proposed for use in some AEDs.

However, there are several instances in which the optimal method of treatment once a defibrillator has been deployed at the emergency scene is to first provide a shock therapy, and not to first provide CPR therapy. Some non-limiting examples of these instances include the following situations.

1. The defibrillator is brought to an emergency scene where the patient has already been receiving CPR. In this instance the action taken in response to the CPR protocol prompts given by a defibrillator with a CPR-first protocol would further delay defibrillation, while it may offer little or no benefit to the patient.

2. A defibrillator is brought to an emergency scene very rapidly, within a few minutes of a patient collapse (about 2-3 minutes). Such a situation may arise in a home rescue situation. In this scenario CPR may not provide any additional benefit, but may compromise patient survival by delaying shock therapy.

3. The person responding to the emergency is not capable of effectively administering CPR. For example, the emotional distress of the emergency may be too great to permit the person to effectively perform CPR. In another example, the responding person may not know how to perform CPR or not remember CPR skills. Or, the responder may simply be physically unable to perform effective CPR. Poorly or inadequately performed CPR may delay defibrillating shock therapy while providing little or no benefit to the patient, and reduce chances of patient survival.

4. The person had an impendent cardiac arrest. Caregivers are already tending to the patient in distress when the cardiac arrest occurs and the AED is already at the scene. It this situation, the patient may benefit more from an immediate shock, rather than from CPR.

In each of these cases, it would be useful to allow the user to move directly to a defibrillation shock protocol. This protocol includes shock analysis and the provision of a defibrillating shock if the shock analysis advises provision of a shock. Thus, it has been conceived to devise a defibrillator with a functionality that allows for the user to bypass or override the CPR routine. Thus the defibrillator configuration can allow for a CPR-first therapy; however, the system allows a user to quickly override this default CPR routine and have the device apply defibrillation shock protocol.

In operation, the overriding system generates an inquiry output upon activation. The query is to determine whether any conditions, such as would indicate a CPR override situation, are present. The queries may be single or multiple.

The inquiry may occur in any of several ways. In one embodiment, the inquiry occurs by voice prompt. In another embodiment, the inquiry question is displayed in text on a display screen of the defibrillator; alternatively, the inquiry is presented in graphical symbolic display. In one preferred embodiment, the inquiry comprises a combination screen display with audio signal. Thus, for example, the defibrillator device may display an inquiry question, and at the moment this is displayed the machine also generates a sound signal. The signal may be any known alerting sound such as a bell, whistle, or electronically generated prompt. The sound signal is chosen so as to help draw the user's attention to the visual display.

In yet another embodiment, the inquiry is performed by the device itself. In that instance the machine may perform the inquiry by performing a routine that analyzes physiological data of the patient. The physiological data can be obtained through electrodes or other sensors applied to the patient that are also coupled to the defibrillator for transmission of data through a hard-wired connection or through other means. Such as for example by radio signal or other wireless communication means.

After issuing the inquiry, the system waits for a response indication to be input. Again, the response to the inquiry may be registered by the defibrillator in any of several ways. In one embodiment, a microphone receives an oral reply. The audio signal is converted to an acceptable electrical/digital format. A voice recognition module, implemented through software, analyzes the signal and records the input signal. It can also determine whether a response has been received.

In another embodiment, the response is manually signaled. A user manipulates one or more input devices such as buttons or touch screens. These input devices may be part of a keypad or keyboard. Alternatively, the buttons may be standalone indicators for quick activation, such as buttons marked "HELP" or "CPR OVERRIDE" or "CPR BYPASS". Preferably, the overriding system allows an operator the option of issuing a single command by which to quickly bypass the CPR protocol and move directly to the electrical therapy protocol.

In still a further embodiment, a response is determined by the device. This response is determined by internal analysis of data received through electrodes or other sensors as mentioned above. In this embodiment, the inquiry may also be an internal inquiry within the controller or device. An output of the inquiry external to the device need not occur.

In one embodiment the system allows some waiting period between the time at which the inquiry is issued and the time for receiving the response. The waiting period can be affected by a number of factors such as the implementation, experience with the device, and the speed of using it. Approximately 2 to 15 seconds is one possible waiting period. If a bypass response has not been input into the device by the expiration of the waiting period, the system proceeds to a CPR function.

If a response is inputted into the system, the response is analyzed. The system determines whether to revert to the default CPR-first protocol or whether to override the CPR-first protocol and proceed to a shock analysis. A negative response, a non-response (delay exceeds waiting period time) or a response other than an affirmative response (a non-affirmative response), may be set to trigger the CPR-first protocol. An affirmative response, in reply to the inquiry, may trigger the CPR override. In a further related embodiment, the system can be set so that when CPR is recommended, if the system does not detect the performance of CPR within a set period of time, e.g. thirty (30) seconds, the CPR protocol is then skipped.

Different embodiments of the defibrillator with overridable CPR-first protocol may generate more than one query. In those embodiments, each query is separately timed. A time delay for any query that exceeds the set time moves the system to the CPR protocol. Additionally, each response to each query is separately analyzed. A triggering response to any of the multiple queries may be a command to override the CPR-first protocol. Thus, for example, in a series of three questions, the user may input answers to the first two questions, each in a timely manner that does not order the system to override the CPR protocol. However, the third answer may indicate an override command. At that point, the system would move to a defibrillation shock protocol—shock analysis and the provision of a defibrillating shock if the shock analysis advises provision of a shock.

Figure 4:
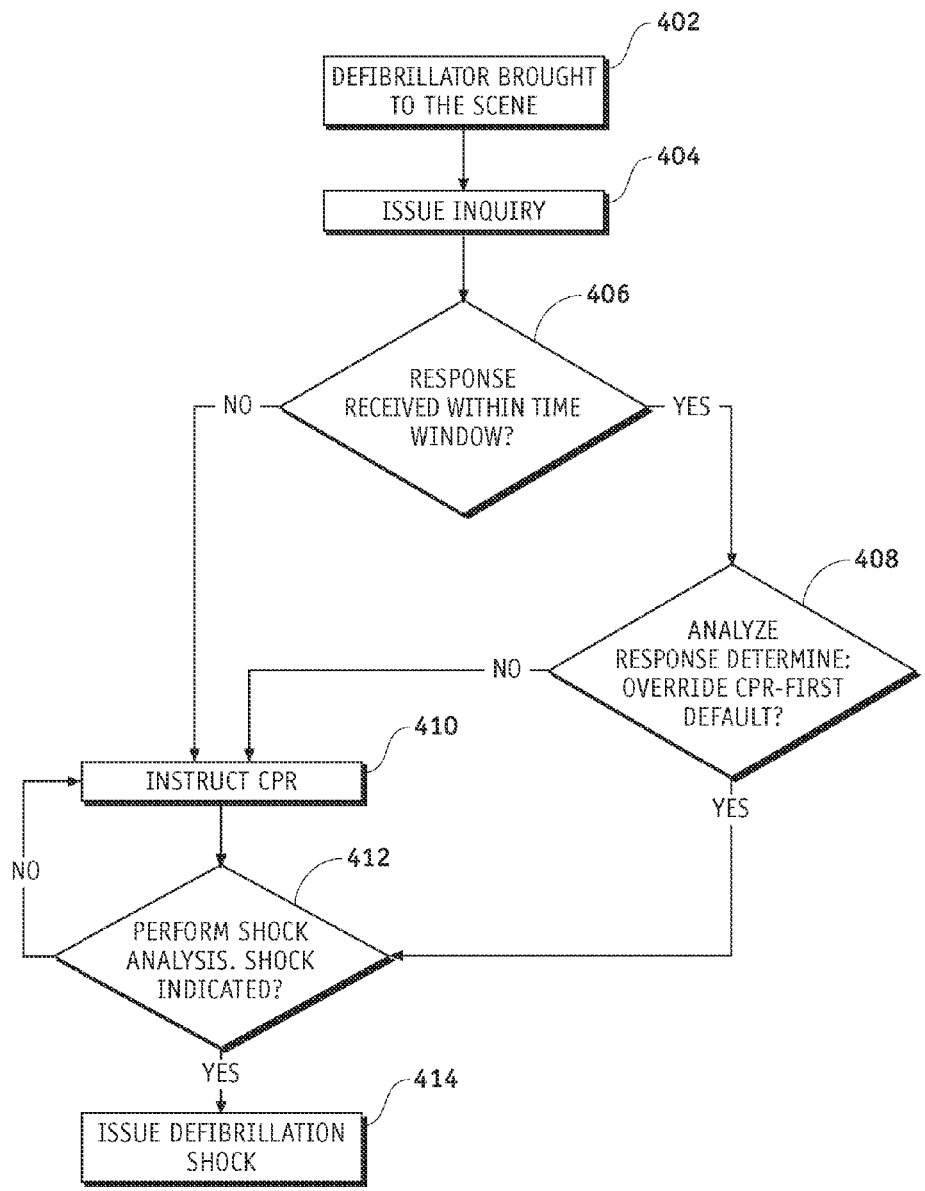
FIG. 4 is a simplified flow chart showing a protocol selection method configured in an external defibrillator in accordance with a first exemplary embodiment of the invention.

Referring to FIG. 4, a flowchart is presented that illustrates a method of operating the external defibrillator of FIG. 2 in accordance with a first exemplary embodiment of the present invention. The method of FIG. 4 may include processing or programming steps programmed into that portion of a defibrillator processing system that allows for a CPR override. The method begins when the defibrillator is brought to the scene of an emergency and activated 402. The activation 402 of the override prompt may begin, for example, when the defibrillator receives indications that electrodes are in place on the patient and data is being received by the machine.

In a next step 404, the system issues an override inquiry. A timing function begins upon issuing the inquiry. As stated above, the inquiry may be issued in any combination of several manners—text, audio signal, voice prompt, etc. In one embodiment, the inquiry is issued at that point in the process when the CPR first protocol is otherwise ready to initiate.

After issuing the inquiry, the system awaits a response 406 for a given period of time. If no response is received when the set time frame expires, the system proceeds to the normal CPR protocol 410. If the system does receive a response within the set time frame, the system analyzes 408 the response. It should be noted that the system may be structured so that once a response is received then the system proceeds immediately to analyze that response in the succeeding step. In other words the system need not wait until the time frame expires before moving on to the next step, assuming a response is input. This is done to minimize the time before a therapy begins. As a practical example, a charging routine involving an internal capacitor need not wait for the entire set time to expire before beginning.

In the next step, the system determines 408 whether the response authorizes a CPR override. If it does not, the system proceeds to the CPR protocol 410. If the response does authorize CPR override, then the system proceeds, bypasses CPR protocols and proceeds to a shock protocol, or other treatment protocol appropriate for the patient state.

Having received a response that authorizes the CPR override, the system next performs a shock analysis 412. In this step, as is known in the defibrillator art, the system determines whether the data received from the patient indicate a defibrillator shock should be applied. If no shock is indicated, then the system proceeds to the CPR protocol 410. Alternatively, if a shock is indicated, then the system applies the appropriate shock to the patient 414.

Figure 5:
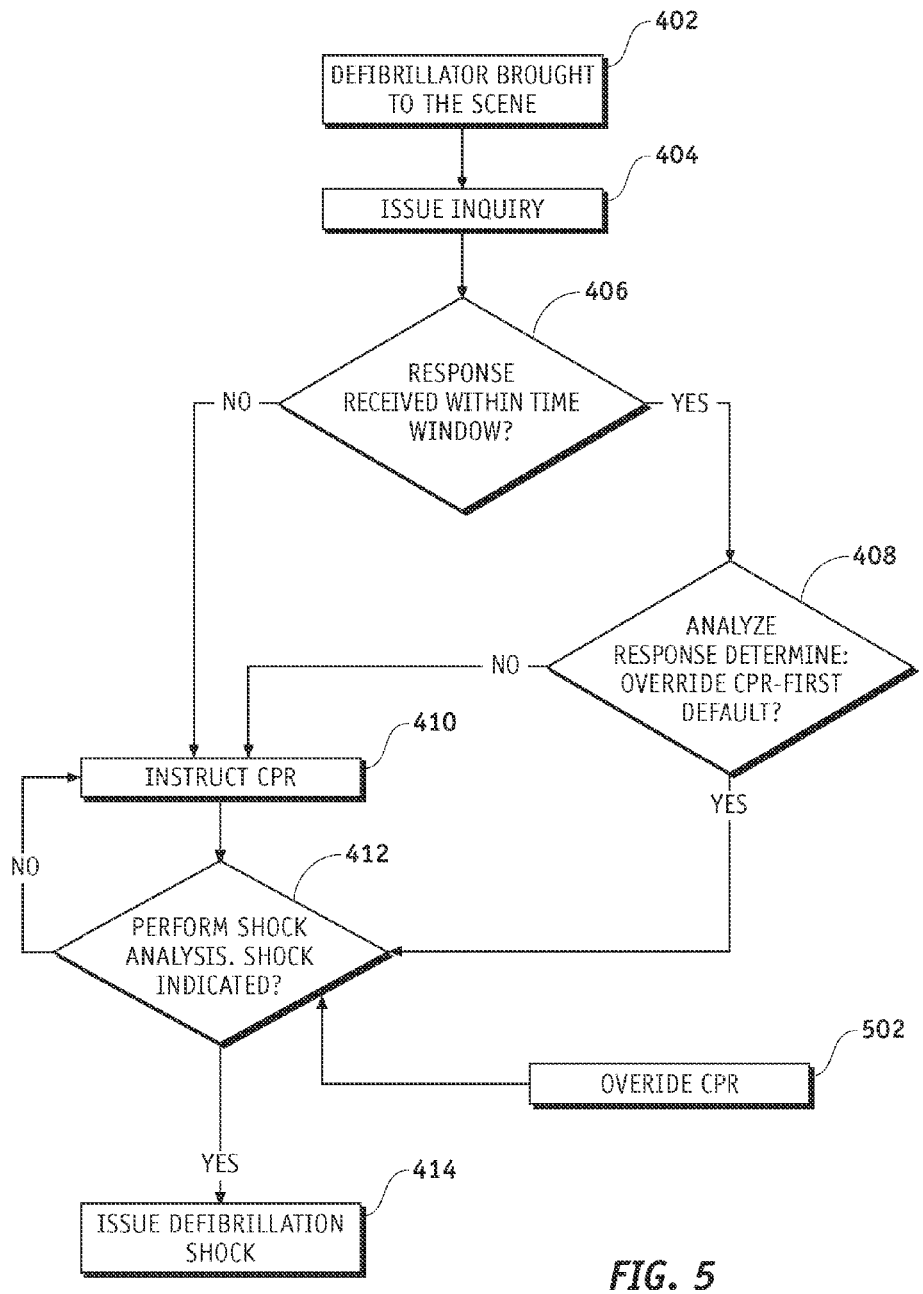
FIG. 5 is a simplified flowchart showing a protocol selection method of operating the external defibrillator of FIG. 2 in accordance with a second exemplary embodiment of the present invention.

In a further embodiment, the system allows for an immediate CPR override. In this embodiment of the system the CPR bypass instruction need not wait for a prompt; instead the system may be commanded to proceed directly to shock mode. Referring to FIG. 5, a flowchart is presented that illustrates a method of operating the external defibrillator of FIG. 2 in accordance with a second exemplary embodiment of the present invention. The system illustrated in FIG. 5 is somewhat similar to the system illustrated in FIG. 4. For example, the system includes many of the same core steps such as issuing an inquiry, waiting for a response, analyzing a response, and the default CPR functionality. However, the system includes a difference shown in the OVERRIDE CPR block 502. This is a command that is independent of the other functionality of the system. Upon receiving this input the system proceeds immediately to the shock mode, and begins, for example with a shock analysis 412.

In operation, some examples of voice or displayed text inquiries, along with corresponding responses to be supplied by the user, include the following non-limiting examples.

1. Has CPR been given so far? (YES/NO) (NO is set as default; if YES, override CPR.)

2. Did the victim collapse less than TMIN ago? (YES/NO) (NO is set as default; if YES, override CPR.)

3. Can you perform CPR? (YES/NO) (if NO, override CPR, YES is set as default.)

The TMIN is set to a value that is deemed to result in benefit to the patient from the therapy sequence resulting from the response to the second inquiry above. The value of TMIN would preferably be in the range of zero (0) to about five (5) minutes.

An alternative implementation of the overridable CPR-first protocol uses a different inquiry format. This format is transparent to the user/rescuer because the answers to the inquiries are provided by the results of analysis of patient physiological data by the defibrillator An example of this is as follows:

2. Is CPR being sensed? (YES/NO) (NO is set as default; if YES, override CPR.)

3. Does the patient have a pulse? (YES/NO) (NO is set as default; if YES, override CPR.)

4. Does the shock analysis algorithm indicate immediate shock is advised? (YES/NO) (NO is set as default, if YES, override CPR.)

It is noted that the use of the system includes situations in which the choice to proceed to a shock protocol is not dependent on ECG analysis. It can result from a response to questions that are input by a user.

In view of the foregoing, it should be appreciated that methods and apparatus are available that allow a defibrillator user to override a CPR-first protocol and move to a shock therapy protocol. This may help to minimize the inherent time delay between defibrillator activation and the administration of a defibrillation shock therapy. While a finite number of exemplary embodiments have been presented in the foregoing detailed description of the invention, it should be appreciated that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road map for implementing exemplary embodiments of the invention. It being understood that various changes may be made in the function and arrangement of elements described in an exemplary embodiment without departing from the scope of the invention as set forth in the appended claims.

The invention claimed is:

1. An external defibrillator for providing a selected treatment protocol to a patient comprising:
a plurality of electrodes affixed to the defibrillator and capable of being attached to a patient so as to provide shock therapy and to provide patient data to the defibrillator;
an input device disposed on the defibrillator;
an output device disposed on the defibrillator; and
a controller disposed in said defibrillator, said controller coupled to said plurality of electrodes, said input device, and said output device, and said controller also configured to:
issue a query as an output;
wait for a response to the query within a set time from the issuance of the query;
order a CPR protocol if no response to the query is received within the set time from the issuance of the query;
analyze a response received within the set time;
order the CPR protocol if the analyzed response is non-affirmative; and
order a shock protocol if the analyzed response is affirmative.

2. The external defibrillator according to claim 1, further comprising an override function configured to cause the controller to select a shock treatment protocol.

3. The defibrillator according to claim 1, in which the output device comprises a screen.

4. The defibrillator according to claim 1, in which the output device comprises a speaker capable of providing audible sound to a defibrillator user.

5. The defibrillator according to claim 4, in which the controller is configured to provide voice prompts through said speaker as a query.

6. The defibrillator according to claim 1, in which the input device comprises a microphone and the controller is configured to recognize voice commands spoken through the microphone as the response.

7. The defibrillator according to claim 1, in which the controller is further configured to receive patient data from the plurality of electrodes as the response to the query.

8. An external defibrillator for providing a selected treatment protocol to a patient comprising:
a plurality of electrodes affixed to the defibrillator and capable of being attached to a patient so as to provide shock therapy and to provide patient data to the defibrillator;
an input device disposed on the defibrillator;
an output device disposed on the defibrillator;
means disposed in said defibrillator for issuing a query;
means disposed in said defibrillator for waiting for a response to the query within a set time from the issuance of the query;
means disposed in said defibrillator for ordering a CPR protocol if no response to the query is received within the set time from the issuance of the query;
means disposed in said defibrillator for analyzing a response received within the set time;
means disposed in said defibrillator for ordering the CPR protocol if the analyzed response is non-affirmative; and
means disposed in said defibrillator for ordering a shock protocol if the analyzed response is affirmative.

9. The defibrillator according to claim 2, in which the controller is configured to implement the override function.

10. The defibrillator according to claim 2, in which the controller is separate from the override function.

11. The external defibrillator according to claim 8, further comprising override means for causing a shock treatment protocol to be selected.

12. The defibrillator according to claim 8, further comprising means for providing audible sound to a defibrillator user.

13. The defibrillator according to claim 8, further comprising means for recognizing voice commands spoken through a microphone as the response.

14. The defibrillator according to claim 8, further comprising means for receiving patient data from the plurality of electrodes as the response to the query.

\* \* \* \* \*